(12) United States Patent
Pearce

(10) Patent No.: US 6,890,883 B2
(45) Date of Patent: May 10, 2005

(54) BIAXIALLY STRETCHED POLYESTER AS A PHOTO-RECEPTIVE LAYER

(75) Inventor: Tony M. Pearce, Alpine, UT (US)

(73) Assignee: EdiZONE, LC, Alpine, UT (US)

( * ) Notice: Subject to any disclaimer, the term of this patent is extended or adjusted under 35 U.S.C. 154(b) by 0 days.

(21) Appl. No.: 10/364,902

(22) Filed: Feb. 11, 2003

(65) Prior Publication Data

US 2004/0009875 A1 Jan. 15, 2004

Related U.S. Application Data

(60) Provisional application No. 60/356,279, filed on Feb. 11, 2002.

(51) Int. Cl.$^7$ .......................... B41M 5/035; B41M 5/38
(52) U.S. Cl. .................... 503/227; 428/480; 428/910
(58) Field of Search .................. 428/480, 910; 503/227; 8/471

(56) References Cited

U.S. PATENT DOCUMENTS

| | | | |
|---|---|---|---|
| 4,510,392 A | 4/1985 | Litt et al. ................. | 250/475.2 |
| 5,223,475 A | 6/1993 | Bloodworth et al. ....... | 503/227 |
| 5,407,893 A * | 4/1995 | Koshizuka et al. ......... | 503/227 |
| 5,495,539 A | 2/1996 | Sieverding .................. | 382/276 |
| 5,496,121 A | 3/1996 | Gunderson ................. | 400/692 |
| 5,555,012 A | 9/1996 | Ellson et al. ............... | 347/217 |
| 5,627,240 A | 5/1997 | Furukawa et al. .......... | 525/384 |
| 5,885,930 A | 3/1999 | Brock et al. ................ | 503/227 |
| 5,933,578 A | 8/1999 | Van de Capelle et al. .. | 395/109 |
| 5,980,588 A | 11/1999 | Valmassoi ...................... | 8/467 |
| 6,019,151 A | 2/2000 | Wen et al. .................. | 156/387 |
| 6,036,099 A | 3/2000 | Leighton .................... | 235/488 |
| 6,146,032 A | 11/2000 | Dunham ................ | 400/120.18 |
| 6,182,571 B1 | 2/2001 | Jolliffe et al. .............. | 101/465 |
| 6,261,012 B1 | 7/2001 | Haas et al. ................. | 400/208 |
| 6,267,052 B1 | 7/2001 | Hill et al. .................... | 101/211 |
| 6,349,181 B1 | 2/2002 | Truc .......................... | 396/661 |
| 6,375,224 B1 | 4/2002 | Truc .......................... | 283/36 |
| 6,409,872 B1 | 6/2002 | Campion et al. ........... | 156/264 |
| 6,412,772 B1 | 7/2002 | Itoh et al. ................... | 271/145 |
| 6,483,607 B1 | 11/2002 | Van de Capelle et al. ... | 358/1.9 |

* cited by examiner

*Primary Examiner*—B. Hamilton Hess
(74) *Attorney, Agent, or Firm*—Daniel P. McCarthy; Parsons Behle & Latimer

(57) ABSTRACT

Methods for using biaxially stretched polyester as a photo-receptive layer for dye sublimation printing are disclosed. Two-sided sublimation printing on polyester is achieved.

25 Claims, 1 Drawing Sheet in # BIAXIALLY STRETCHED POLYESTER AS A PHOTO-RECEPTIVE LAYER

CROSS REFERENCE TO RELATED APPLICATIONS

PRIORITY: I hereby claim the benefit under Title 35, U.S.C. § 119(e) of a U.S. Provisional Patent Application filed on Feb. 11, 2002 and having Ser. No. 60/356,279.

BACKGROUND

In the prior art, some effort has been made to laminate photographs or place them into plastic casings for protection. Digital photographs are often printed on special paper or paper or polymer film which is polymer coated with polyester or other polymers. However, such papers must be made flexible in order to go through the dye sublimation printers for which they are designed. They are also not made to have photographs on both sides. Another drawback is that the polyester or polymer coating is very thin, and thus the photograph can lack depth and luster.

SUMMARY

Biaxially stretched polyester as a photo-receptive layer is disclosed.

DETAILED DESCRIPTION

Figure 1:
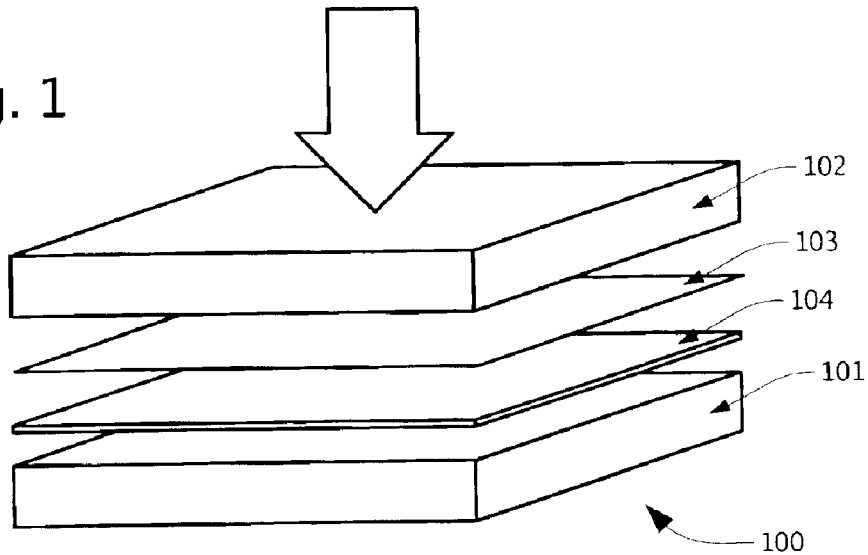
FIG. 1 depicts a sublimation printing process using biaxially stretched polyester as a photo-receptive layer as disclosed herein.

As used herein, "BSP" shall mean biaxially stretched polyester. In the past, there has not been any use of BSP films as a photo-receptive layer for printing photographs. I have discovered that the use of a clear BSP film (which is considerably thicker than the coated films of prior art photo paper) as the photo-receptive layer on top of a white substrate provides marvelous color, clarity, detail, and depth to photos and other graphics printed by dye sublimation.

Printing of a photograph or other graphic onto BSP may be achieved by use of heat and/or pressure over time in order to sublimate onto the laminate. The heat and/or pressure can be applied in a flat heat press, or in a printer such as known dye sublimation printers, or in a heated roller press, or by any other means. The laminate may include a white layer, such as BSP or biaxially stretched poly(ethylene) naphthalate (BSPN), and a layer of clear BSP or BSPN on one or both sides of the white layer. The thickness or material of the white layer can be any thickness or material that provides reasonable opacity and brightness. For a feeling of durability and quality, the center layer is may be 0.001 to 0.014 inches, such as 0.008 inch thick BNP, but can be much thinner and can be thicker. BNP is commercially available at this time in thicknesses up to 0.014 inches. The BSP or BSPN layer can be as thin as 0.0001 inches, which is considerably thicker than the coatings on prior art paper. More commonly, the BSP or BSPN layer may be about 0.001 inches.

For some applications, such as scrapbooking and photo albums, the BSP or BSPN photo-receptive layers may be on both sides of the laminate. For example, a heat press 100 including twin platens 101 and 102 as shown in FIG. 1 presses printed transfer paper 103 containing an image or graphic onto the laminate 104. After a desired time period, such as about 1 to 600 seconds, at a desired temperature, such as about 200 to 600 degrees F., at a desired pressure, such as about 2 to 1,000 p.s.i., the laminate is removed and a beautiful graphic is embedded in the photo-receptive layer on the side of the laminate that was facing the transfer paper. The process may then be repeated with a new piece of transfer paper with the three-layer laminate 104 being turned over resulting in a laminate with a beautiful image on each of its two sides. When placed in a notebook or binder, successive pages of facing images are presented. This eliminates the need for placing photos onto both sides of a punched paper.

The durability of the BSP or BSPN also eliminates the need for protective slip covers on the pages. Such graphics can be put in frames or any other place photos are used, or can be used alone if made three-dimensionally stiff. The white or light 'layer' of the laminate can be any item, including three-dimensional items, for example a white marble gravestone. There are many white and clear BSP and BSPN films commonly available, from suppliers such as Dupont, Teijin, and Filmquest.

Lamination can be done by several methods. One method is to co-extrude the white and clear layers together by means known in the field. Another means is by adhesive lamination of separately produced clear and white films. Another means is by coextruding an interlayer of polymer onto either the white or clear films or both, then heat laminating the layers together by means known in the field. For a three-dimensional white 'layer', the clear film could be coextruded with adhesive or a meltable polymer and then applied to the white substrate 'layer'. Any means of lamination is acceptable.

Another embodiment coats the back of a clear BSP or BSPN film with a white material. For example, flood coating can be used. Or, the clear film can be dye sublimated and then the back can be coated by the end user with a peel-and-stick white layer or even painted white. The laminate can have any number of layers or coatings, provided the photo-receptive layer is BSP or BSPN or other bi-axially stretched polymeric films and is backed directly or indirectly with a white or light layer that makes the sublimated graphic show up acceptably. For a very stiff laminate, for example, two layers of 0.014 inch thick BSP plus one or two clear BSP or BSPN or the like outer layer(s) could be laminated together. This could be used for signage, for example, or for durable recording of wedding photos, or for a photo that could be placed on a desk with only a stick-on stand but no frame.

The biaxial stretching is important in that it provides crystallinity to the polymer; otherwise, the transfer paper may stick to the polymer or the polymer may deform under the heat of dye sublimation.

While the methods, structures and formulations have been described and illustrated in conjunction with a number of specific examples, those skilled in the art will appreciate that variations and modifications may be made without departing from the principles herein illustrated, described, and claimed. The present invention, as defined by the appended claims, may be embodied in other specific forms without departing from its spirit or essential characteristics. The configurations of lights described herein are to be considered in all respects as only illustrative, and not restrictive. All changes that come within the meaning and range of equivalency of the claims are to be embraced within their scope.

What is claimed is:

1. A method for dye sublimation printing of photographs or graphics onto biaxially stretched polyester comprising the steps of:

obtaining a quantity of biaxially stretched polyester ("BSP") that has some crystallinity in its polymers in order to reduce any inherent tendency of said BSP to adhere to a sheet of transfer paper during a dye sublimation printing process, said BSP being a clear film having a thickness of from about 0.0001 to about 0.014 inches, selecting a white substrate, laminating said BSP clear film to said white substrate to produce a laminate with a BSP clear layer, said white substrate and said BSP remaining adjacent each other while carrying out said dye sublimation printing, said white substrate being of a thickness that affords relative light opacity to said substrate, selecting a piece of transfer medium containing a photograph or graphic for dye sublimation printing, disposing said transfer paper against said BSP clear layer of said laminate, disposing said transfer paper and said BSP clear layer of said laminate in a press, closing said press to apply pressure to said transfer medium and said BSP clear layer of said laminate, causing said transfer paper and said BSP clear layer of said laminate to be exposed to heat, keeping said press closed for a desired time period in order to cause a photograph or graphic image on said transfer paper to be transferred to said BSP clear layer of said laminate by dye sublimation printing, opening said press, and removing said laminate to reveal a printed image.

2. A method as recited in claim 1 wherein said pressure is at least about 2 p.s.i.

3. A method as recited in claim 1 wherein said heat is at least about 200 degrees F.

4. A method as recited in claim 1 wherein said time period is at least about 1 second.

5. A method as recited in claim 1 wherein said laminate is selected from the group consisting of a layer of clear BSP on a layer of white BSP and a layer of clear biaxially stretched poly(ethylene) naphthalate ("BSPN") on a layer of white BSPN.

6. A method as recited in claim 1 wherein said laminate includes a layer of clear BSP on a layer of white BSPN.

7. A method as recited in claim 1 wherein said laminate includes a layer of clear BSPN on a layer of white BSP.

8. A method as recited in claim 1 wherein said substrate of said laminate has a thickness in the range of 0.001 to 0.014 inches.

9. A method as recited in claim 1 wherein said substrate of said laminate has a thickness in the range of about 0.008 inch thick.

10. A method as recited in claim 1 wherein said BSP clear film is about 0.001 inches thick.

11. A method as recited in claim 1 wherein said white substrate has a layer of clear film BSP on each of its two sides for double sided printing.

12. A method as recited in claim 1 further comprising applying a second BSP clear layer to said laminate on a side of said laminate opposite said previously applied BSP clear layer.

13. A method as recited in claim 12 further comprising the steps of:

selecting a second piece of transfer paper bearing an image, disposing said second piece of transfer paper adjacent said second BSP clear layer, applying heat and pressure to said second piece of transfer paper and said second BSP clear layer to cause dye sublimation printing of the image on said second piece of transfer paper onto said second BSP layer to produce laminated polyester with two-sided dye sublimation printed images.

14. A method for dye sublimation printing of photographs or graphics onto biaxially stretched polymer film comprising the steps of:

obtaining a quantity of laminate that has a white substrate and a clear film located on said white substrate, said clear film being biaxially stretched polymer film selected from the group consisting of BSP and BSPN, said clear film having some crystallinity in its polymers in order to reduce any inherent tendency of said clear film adhere to a sheet of transfer paper during a dye sublimation printing process, said white substrate being of a thickness that affords relative light opacity to said substrate, and transferring a photographic or graphic image into the clear film by means of dye sublimation.

15. A method as recited in claim 14 wherein the dye sublimation transfer is accomplished by means of a flat heat press, a printer, or a heated roller press.

16. A method as recited in claim 15 wherein said dye sublimation transfer involves a temperature of at least about 200 degrees F.

17. A method as recited in claim 15 wherein said dye sublimation transfer involves a time period under heat and/or pressure of at least about 1 second.

18. A method as recited in claim 14 wherein said laminate is selected from the group consisting of a layer of clear BSP on a layer of white BSP and a layer of clear BSPN on a layer of white BSPN.

19. A method as recited in claim 14 wherein said laminate includes a layer of clear BSP on a layer of white BSPN.

20. A method as recited in claim 14 wherein said laminate includes a layer of clear BSPN on a layer of white BSP.

21. A method as recited in claim 14 wherein said substrate of said laminate has a thickness in the range of 0.001 to 0.014 inches.

22. A method as recited in claim 14 wherein said substrate of said laminate has a thickness in the range of about 0.008 inch thick.

23. A method as recited in claim 14 wherein said film of said laminate is about 0.001 inches thick.

24. A method as recited in claim 14 wherein said white substrate of said laminate has a layer of clear film BSP on each of its two sides for double sided printing.

25. A method as recited in claim 24 wherein said laminate has a layer of clear film on each of its two side and further comprising the step of transferring a photographic or graphic image into said second BSP clear layer by means of dye sublimation to produce laminated polyester with two-sided dye sublimation printed images.

* * * * *